US011446266B2

(12) United States Patent
Atkinson

(10) Patent No.: US 11,446,266 B2
(45) Date of Patent: Sep. 20, 2022

(54) COMBINATION COMPOSITION

(71) Applicant: AFT Pharmaceuticals Limited, Auckland (NZ)

(72) Inventor: Hartley C. Atkinson, Auckland (NZ)

(73) Assignee: AFT Pharmaceuticals Limited, Takapuna (NZ)

( * ) Notice: Subject to any disclaimer, the term of this patent is extended or adjusted under 35 U.S.C. 154(b) by 0 days.

(21) Appl. No.: 16/149,109

(22) Filed: Oct. 1, 2018

(65) Prior Publication Data

US 2019/0029982 A1 Jan. 31, 2019

Related U.S. Application Data

(63) Continuation of application No. 14/832,154, filed on Aug. 21, 2015, now abandoned, which is a continuation of application No. 13/882,953, filed as application No. PCT/NZ2011/000226 on Oct. 26, 2011, now abandoned.

(30) Foreign Application Priority Data

Nov. 4, 2010 (NZ) ........................................ 589011

(51) Int. Cl.

| | |
|---|---|
| ***A61K 31/192*** | (2006.01) |
| ***A61K 31/167*** | (2006.01) |
| ***A61K 47/18*** | (2017.01) |
| ***A61K 9/00*** | (2006.01) |
| ***A61K 9/08*** | (2006.01) |
| ***A61P 29/00*** | (2006.01) |

(52) U.S. Cl.

CPC .......... *A61K 31/192* (2013.01); *A61K 9/0019* (2013.01); *A61K 9/08* (2013.01); *A61K 31/167* (2013.01); *A61K 47/183* (2013.01); *A61P 29/00* (2018.01)

(58) Field of Classification Search

CPC .............. A61K 2300/00; A61K 31/192; A61K 31/167; A61K 9/0019; A61K 47/183; A61K 9/08

See application file for complete search history.

(56) References Cited

U.S. PATENT DOCUMENTS

| | | | | |
|---|---|---|---|---|
| 2008/0103206 A1 | 5/2008 | Swann et al. | | |
| 2008/0275125 A1 | 6/2008 | Atkinson | | |
| 2008/0200549 A1 | 8/2008 | Atkinson | | |
| 2009/0264530 A1* | 10/2009 | Nickell | ................ A61K 31/167 514/568 | |

FOREIGN PATENT DOCUMENTS

| | | | |
|---|---|---|---|
| CN | 1758904 | 4/2006 | |
| JP | 2005510510 | 4/2005 | |
| KR | 2006/0072839 | 6/2006 | |
| WO | WO1997020551 | 6/1997 | |
| WO | WO-2006004449 A2 * | 1/2006 | ............. A61K 31/16 |
| WO | WO2008/079818 | 7/2008 | |
| WO | WO2010044681 | 4/2010 | |
| WO | WO2010105129 | 9/2010 | |
| WO | WO2012/005605 | 1/2012 | |

OTHER PUBLICATIONS

Moller et al., British Journal of Anaesthesia 94 (5): 642-8 2005. (Year: 2005).*

Westhuizen et al., Anaesth Intensive Care 2011; 39: 242-246. (Year: 2011).*

Smith et al., Pain Medicine, vol. 12, Issue 6, Jun. 2011, pp. 961-981 (Year: 2011).*

International Search Report for PCT/NZ2011/000226 dated Mar. 28, 2012.

Written Opinion for PCT/NZ2011/000226 dated Mar. 28, 2012.

International Preliminary Report on Patentability for PCT/NZ2011/000226 dated May 8, 2013.

Antman et al., "Use of Nonsteroidal Antiinflammatory Drugs: An Update for Clinicians: A Scientific Statement for the American Heart Association," Circulation, pp. 1634-1642 (2007).

Hinz et al., "Acetaminophen (paracetamol) is a selective cyclooxygenase-2 inhibitor in man," The FASEB Journal, 22(2):383-390 (2008).

http://medical-dictionary.thefreedictionary.com/unit-dose, accessed on May 17, 2015.

Bookstaver et al., J Pain Res 2010, 3:67-79, Published online May 25, 2010.

Rainsford et al. (J. Pharm. Pharmacology, vol. 49, p. 345-376 (1996).

Bookstaver et al., "Intravenous ibuprofen: the first injectable product for the treatment of pain and fever," Journal of Pain Research, May 2010 3:67-79.

Merry et al., "Combined acetaminophen and ibuprofen for pain relief after oral surgery in adults: a randomized controlled trial," British Journal of Anaesthesia, Jan. 2010, 104(1):80-88.

* cited by examiner

*Primary Examiner* — Jean P Cornet

(74) *Attorney, Agent, or Firm* — Fish & Richardson P.C.

(57) ABSTRACT

An intravenous composition for providing relief for pain and/or inflammation, the composition having ibuprofen and paracetamol in combination for delivering to a human at each dose: a) approximately 125 mg to approximately 175 mg ibuprofen in combination with approximately 475 mg to approximately 525 mg paracetamol; or b) approximately 275 mg to approximately 325 mg ibuprofen in combination with approximately 975 mg to approximately 1,025 mg paracetamol.

4 Claims, No Drawings

COMBINATION COMPOSITION

CROSS-REFERENCE TO RELATED APPLICATIONS

This application is a continuation application of U.S. application Ser. No. 14/832,154, filed Aug. 21, 2015, which is a continuation application of U.S. application Ser. No. 13/882,953, filed May 1, 2013, which is the national phase under 35 U.S.C. § 371 of PCT International Application No. PCT/NZ2011/000226, filed Oct. 26, 2011, which claims the benefit of New Zealand Patent Application No. 589011, filed Nov. 4, 2010, the entire contents of the aforementioned applications are hereby incorporated herein by reference.

FIELD OF INVENTION

This invention relates to a combination composition comprising paracetamol and ibuprofen. A particularly preferred embodiment of the invention relates to a combination composition containing these active ingredients for use in relieving pain and/or inflammation.

BACKGROUND

Combinations of paracetamol and ibuprofen are known, for example as relatively low dose tablets having 150 mg ibuprofen and 500 mg paracetamol. However there is a need for a medication, particularly one which can be administered intravenously in a hospital environment. It is an object of an embodiment of the present invention to go at least some way towards facilitating this.

DEFINITIONS

References in this specification to an adult mean a person weighing 50 kg or more.

References in this specification to a child mean a person weighing less than 50 kg.

While ibuprofen and paracetamol are specifically referred to in this specification, suitable other pharmaceutically acceptable forms of these two actives (eg salts, etc) may also be used and are intended to be embraced in the claims by references to the actives per se, with the weight amounts adjusted accordingly. For example, when a salt form is used, sufficient quantity may be included to meet the desired amount of the compound per se (eg, 513 mg ibuprofen lysinate, or 553 mg ibuprofen arginine salt, corresponds with 300 mg ibuprofen). Thus, for example, a reference to 300 mg ibuprofen may be construed as sufficient to embrace the therapeutically equivalent amount of ibuprofen lysinate or ibuprofen arginine.

The term "comprising" and derivatives thereof, eg "comprises", if and when used in relation to a combination of features should not be taken to exclude the possibility of the combination having further unspecified features.

SUMMARY OF INVENTION

According to one aspect of the invention there is provided an intravenous composition for providing relief for pain and/or inflammation, the composition having ibuprofen and paracetamol in combination for delivering to a human at each dose:

a) approximately 125 mg to approximately 175 mg ibuprofen in combination with approximately 475 mg to approximately 525 mg paracetamol; or b) approximately 275 mg to approximately 325 mg ibuprofen in combination with approximately 975 mg to approximately 1,025 mg paracetamol.

Preferably the composition is for dosing on approximately a 6 hourly basis.

Preferably the composition comprises:

a) approximately 150 mg ibuprofen in combination with approximately 500 mg paracetamol; or b) approximately 300 mg ibuprofen in combination with approximately 1,000 mg paracetamol.

Preferably the composition is in the form of a solution.

A further aspect of the invention comprises the use of paracetamol and ibuprofen in the manufacture of an intravenous medicament for treating pain and/or inflammation in a human wherein the medicament comprises, on a per dose basis:

a) approximately 125 mg to approximately 175 mg ibuprofen in combination with approximately 475 mg to approximately 525 mg paracetamol; or b) approximately 275 mg to approximately 325 mg ibuprofen in combination with approximately 975 mg to approximately 1,025 mg paracetamol.

Preferably the composition is for dosing on approximately a 6 hourly basis

Preferably the composition comprises:

a) approximately 150 mg ibuprofen in combination with approximately 500 mg paracetamol; or b) approximately 300 mg ibuprofen in combination with approximately 1,000 mg paracetamol.

Preferably the composition is in the form of a solution.

A further aspect of the invention comprises a method of treating pain and/or inflammation by administering to a human, intravenously, a medicament comprising:

a) approximately 125 mg to approximately 175 mg ibuprofen in combination with approximately 475 mg to approximately 525 mg paracetamol; or b) approximately 275 mg to approximately 325 mg ibuprofen in combination with approximately 975 mg to approximately 1,025 mg paracetamol.

Preferably the composition is administered on a 6 hourly basis.

Preferably the composition comprises:

a) approximately 150 mg ibuprofen in combination with approximately 500 mg paracetamol; or b) approximately 300 mg ibuprofen in combination with approximately 1,000 mg paracetamol.

Preferably the composition is in the form of a solution.

DETAILED DESCRIPTION

In a preferred embodiment of the invention an intravenous solution is provided for use in treating pain or inflammation in human patients. The solution is a combination medication comprising ibuprofen, paracetamol and suitable excipients as will be known to those with ordinary skills in the art of formulating intravenous medicines. The excipients may include suitable antioxidants, pH modulators, buffering agents isotonicity agents and purified water.

The following examples illustrate preferred embodiments of the invention in the form of intravenous infusion solutions.

| Ingredient | Example 1 mg/100 ml vial | Example 2 mg/100 ml vial |
|---|---|---|
| Ibuprofen | 150 | 300 |
| Paracetamol | 500 | 1,000 |

For each of the above examples the two active ingredients are mixed with suitable standard excipients to give the vial volumes indicated above.

The infusion solutions are for delivery to a patient as a full dose, for example in each case the patient receives the complete vial contents as a 15 minute infusion every 6 hours. Example 1 is a child's dose and Example 2 is an adult dose. In the case of very young or small children only part of the vial contents of Example 1 may be dosed on a body weight basis, commensurate with instructions from the prescribing physician.

Paracetamol at 4,000 mg per 24 hour period, taken in 4 doses of 1,000 mg every 6 hours, has long been considered sufficient for relieving low level pain but for many patients suffering significant pain, for example in some post operative situations, it is not sufficient. However it is generally not advisable to dose paracetamol at more than 1,000 mg per dose or at more than 4,000 mg per 24 hour period, because to do so can lead to undesirable side effects.

It is known to treat severe pain with ibuprofen in doses of 800 mg every 8 hours. However, doses as high as 800 mg can lead to undesirable side effects, for example adverse cardio renal conditions, renal problems, thrombotic risks and gastrointestinal bleeding. Reducing the amount of ibuprofen at each dosing event may reduce the risk of side effects but at the same time may provide substantially less pain relief.

Surprisingly, an intravenous medicine comprising 150 mg or 300 mg ibuprofen, plus 500 mg or 1,000 mg paracetamol, respectively, for use every 6 hours, provides adequate pain relief for some patients that would otherwise need to take, respectively, 400 mg or 800 mg every 8 hours. The lower dose of ibuprofen reduces the risk of undesirable side effects in some patients but the effectiveness of the medication for such patients is not compromised due to the presence of the paracetamol. This is unexpected because for many patients one would not predict the presence of paracetamol to assist to any significant degree. The combination is counterintuitive because, for example, 400 mg ibuprofen for relief of pain is generally seen as an 8 hourly medicament, and 1,000 mg paracetamol is generally seen as a 6 hourly medicament. The normal dosage regimens for these active ingredients are out of step with one another, ie 8 hourly versus 6 hourly, and thus to the normally skilled artesian they would not, at the doses of the present invention, be seen as suitable for a combination medication.

Similar considerations apply in the case of 150 mg ibuprofen, in combination with 500 mg paracetamol, for treating children suffering from pain. In this regard, surprisingly, some children that would normally be given 200 mg ibuprofen for pain can be given, as an alternative, 150 mg ibuprofen in combination with 500 mg paracetamol.

Administering an intravenous combination solution comprising 300 mg ibuprofen plus 1,000 mg paracetamol to an adult, or an intravenous combination solution comprising 150 mg ibuprofen plus 500 mg paracetamol to a child, on an ongoing basis, for example every 6 hours, provides a surprising level of pain relief compared to administering the same doses orally, for example by way of a tablet. The intravenous administration reduces the need for rescue pain relief in at least some patients recovering from surgical procedures. The intravenous administration may for example be by way of injection or infusion.

Example 3

In a particular embodiment of the invention an intravenous solution may be prepared by mixing the following active ingredients and excipients:

| | AMOUNT |
|---|---|
| ACTIVE INGREDIENTS | |
| Paracetamol | 1000 mg |
| Ibuprofen arginine | 553 mg |
| EXCIPIENTS | |
| Reduced glutathione (as antioxidant) | 20 mg |
| Sodium hydroxide or hydrochloric acid (as a pH modulator) | sufficient to give a pH of 5-6 |
| Sodium citrate (as a buffering agent) | 10 mg |
| Sodium chloride (as an isotonicity agent) | sufficient to impart isotonicity |
| Purified water | Sufficient to bring the composition to 100 ml |

The solution is for administration to an adult as a single intravenous dose and further equivalent doses may be repeated every 6 hours if need be, commensurate with instructions from the prescribing physician.

Example 4

In a further embodiment of the invention an intravenous solution may be prepared by mixing the following active ingredients and excipients:

| | AMOUNT |
|---|---|
| ACTIVE INGREDIENTS | |
| Paracetamol | 500 mg |
| Ibuprofen arginine | 276.5 mg |
| EXCIPIENTS | |
| Reduced glutathione (as antioxidant) | 10 mg |
| Sodium hydroxide or hydrochloric acid (as a pH modulator) | sufficient to give a pH of 5-6 |
| Sodium citrate (as a buffering agent) | 5 mg |
| Sodium chloride (as an isotonicity agent) | sufficient to impart isotonicity |
| Purified water | Sufficient to bring the composition to 100 ml |

The solution is for administration to a child as a single intravenous dose and further equivalent doses may be repeated every 6 hours if need be, commensurate with instructions from the prescribing physician.

While some preferred forms of the invention have been described by way of example it should be appreciated that modifications and improvements can occur without departing from the scope of the following claims.

The invention claimed is:

1. A method of treating pain by administering to a human, intravenously, an aqueous solution comprising:

a) 150 mg ibuprofen in combination with 500 mg paracetamol; or a) 300 mg ibuprofen in combination with 1000 mg paracetamol.

2. The method according to claim 1, wherein the composition is administered on a 6 hourly basis.

3. The method of claim 1 wherein the medicament comprises 150 mg ibuprofen in combination with 500 mg paracetamol.

4. The method of claim 1 wherein the medicament comprises 300 mg ibuprofen in combination with 1000 mg paracetamol.

* * * * *